US00PP26742P2

(12) United States Plant Patent
van Noort

(10) Patent No.: US PP26,742 P2
(45) Date of Patent: May 17, 2016

(54) ***GERANIUM* PLANT NAMED 'NOORTLILAC'**

(50) Latin Name: *Geranium cinereum*
Varietal Denomination: Noortlilac

(71) Applicant: Marco van Noort, Warmond (NL)

(72) Inventor: Marco van Noort, Warmond (NL)

(73) Assignee: Marco van Noort Breeding BV, Warmand (NL)

( * ) Notice: Subject to any disclaimer, the term of this patent is extended or adjusted under 35 U.S.C. 154(b) by 15 days.

(21) Appl. No.: 14/544,140

(22) Filed: Dec. 2, 2014

(51) Int. Cl.
*A01H 5/02* (2006.01)

(52) U.S. Cl.
USPC ..... Plt./324

(58) Field of Classification Search
USPC ..... Plt./324
CPC ..... A01H 5/02; A01H 5/0277
See application file for complete search history.

*Primary Examiner* — Kent L Bell
(74) *Attorney, Agent, or Firm* — Penny J. Aguirre

(57) ABSTRACT

A new cultivar of *Geranium cinereum*, 'Noortlilac', that is characterized by its relatively large flowers that are dark lilac in color with conspicuous dark purple colored veins that are consistent in color throughout the plant and its better resistance to soil fungi relative to other *Geranium cinereum* cultivars.

2 Drawing Sheets

Botanical classification: *Geranium cinereum.*
Cultivar designation: 'Noortlilac'.

BACKGROUND OF THE INVENTION

The present invention relates to a new and distinct cultivar of *Geranium* plant, botanically known as *Geranium cinereum*. 'Noortlilac' and will be referred to hereafter by its cultivar name, 'Noortlilac'.

'Noortlilac' was derived from a breeding program conducted by the Inventor in Warmond, The Netherlands. The objectives of the breeding program were to develop new cultivars of *Geranium cinereum* in a range of flower colors that commence bloom early in the season and exhibit disease resistance, compact plant habits and rain resistance.

'Noortlilac' arose from a cross made in summer of 2010 between an unnamed and unpatented proprietary seedling of *Geranium cinereum* from the Inventor's breeding program as the female parent and *Geranium cinereum* 'Laurence Flatman' (not patented) as the male parent. The Inventor selected 'Noortlilac' as a single unique plant amongst the seedlings that resulted from the above cross in May of 2012.

Asexual propagation of the new cultivar was first accomplished by in vitro propagation by the Inventor in Otrebusy, Poland in April of 2014. Asexual propagation by in vitro propagation and root cuttings has determined that the characteristics of the new cultivar are stable and are reproduced true to type in successive generations.

SUMMARY OF THE INVENTION

The following traits have been repeatedly observed and represent the characteristics of 'Noortlilac'. These attributes in combination distinguish 'Noortlilac' as a new and distinct cultivar of *Geranium.*

1. 'Noortlilac' exhibits relatively large flowers that are dark lilac in color with conspicuous dark purple colored veins.

2. 'Noortlilac' exhibits greater resistance to soil fungi relative to other *Geranium cinereum* cultivars.
3. 'Noortlilac' exhibits flowers that are consistent in color throughout the plant.

The female parent of 'Noortlilac' differs from 'Noortlilac' in having flowers that are smaller in size with inconspicuous flower petal veins and variability in flower coloration. The male parent of 'Noortlilac', 'Laurence Flatman', differs from 'Noortlilac' in having flowers that are smaller in size, lighter in color, and show variability in flower coloration. 'Noortlilac' can also be compared to the *Geranium cinereum* cultivar, 'Ballerina' (not patented). 'Ballerina' is similar to 'Noortlilac' in overall plant shape. 'Ballerina' differs from 'Noortlilac' in having flowers that are smaller in size and lighter in color.

BRIEF DESCRIPTION OF THE DRAWINGS

The accompanying colored photographs illustrate the overall appearance and distinct characteristics of the new *Geranium*. The photographs were taken of a one year-old plant of 'Noortlilac' as field grown in Warmond, The Netherlands and place in a container for the photographs.

The photograph in FIG. 1 provides an overall view of a plant of 'Noortlilac' in bloom.

Figure 1:
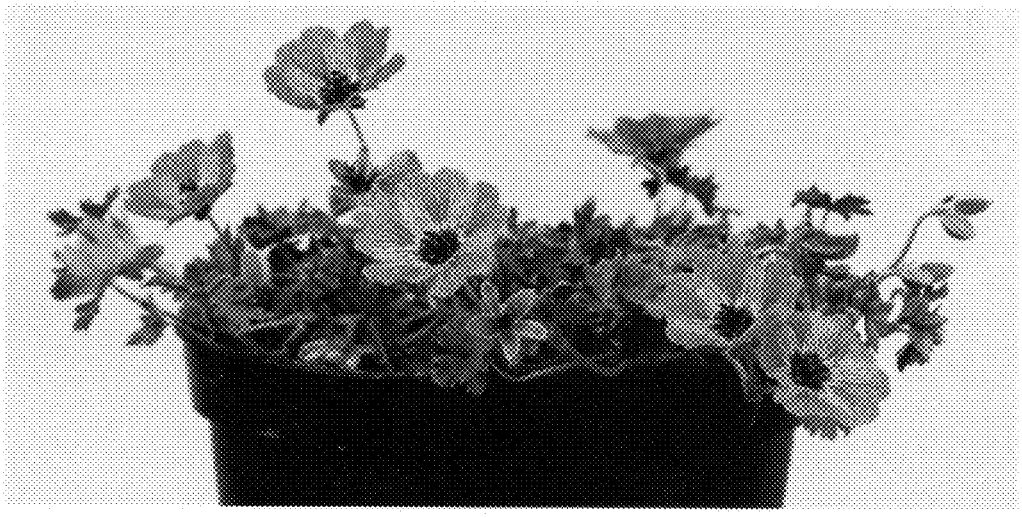
Figure 2:
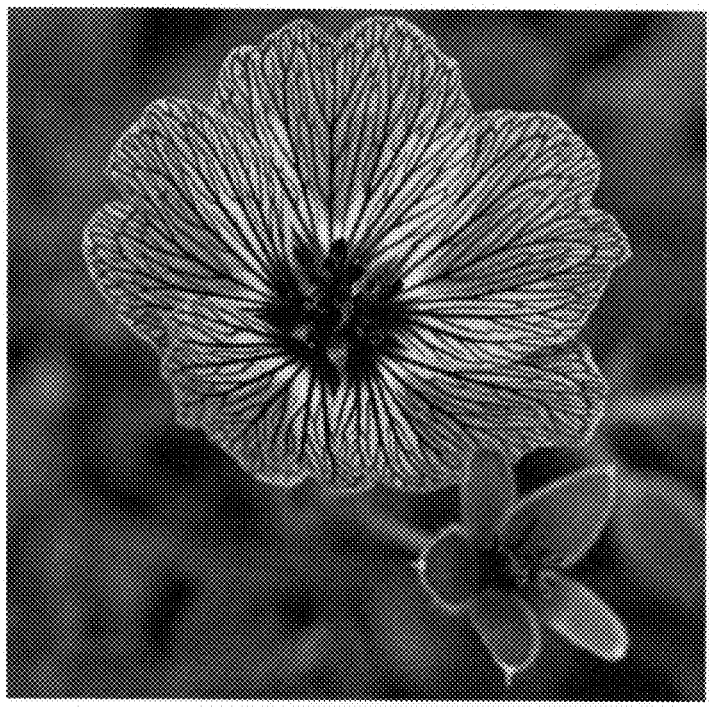

The photograph in FIG. 2 provides a close-up view of a flower of 'Noortlilac'.

Figure 3:
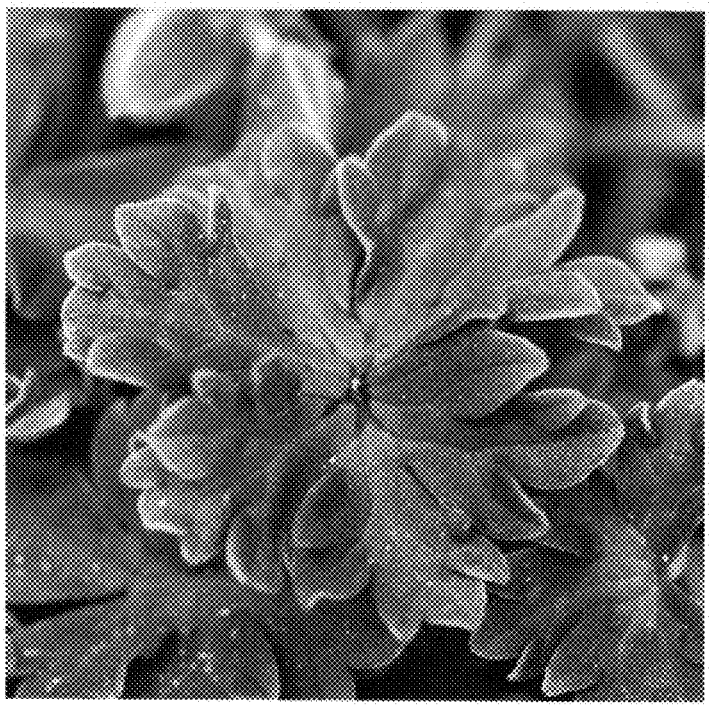

The photograph in FIG. 3 provides a close-up view of the foliage of 'Noortlilac'.

The colors in the photographs are as close as possible with the digital photography techniques available and the color values cited in the detailed botanical description accurately describe the colors of the new *Geranium.*

DETAILED BOTANICAL DESCRIPTION OF THE PLANT

The following is a detailed description of one year-old plants of the new cultivar as field grown in Warmond, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period.*—April into June in The Netherlands.

*Plant type.*—Herbaceous perennial.

*Plant habit.*—Low growing, spreading, and flattened (not mounded).

*Height and spread.*—An average of 15 cm in height and 25 cm in spread as a one year-old plant grown in a field.

*Cold hardiness.*—At least to U.S.D.A. Zone 5.

*Diseases.*—Observed to have some resistance to soil fungi caused by *Botrytis cinerea* and *Pythium* spp.).

*Root description.*—Fibrous and fine, primarily N167B in color.

*Root development.*—An average of 20 weeks to fully develop from a rooted cutting in a 9-cm container.

*Growth rate.*—Moderate, an average of 8 cm per month in spring.

*Propagation.*—In vitro propagation (preferred) and root cuttings.

Stem description:

*Stem size.*—Average of 10.6 cm in length and 2.5 mm in width.

*Stem shape.*—Round.

*Stem color.*—144B with upper side (sun exposed) slightly tinged with 174A.

*Stem surface.*—Slightly glossy with stems moderately covered with very short soft adpressed hairs; average of 0.3 mm in length and too small to measure color.

*Stem strength.*—Moderately strong.

*Internode length.*—Average of 5.6 cm.

*Branching.*—Freely branched with an average of 12 lateral branches.

Foliage description:

*Leaf shape.*—Reniform (in outline), palmately deeply cleft to parted with an average of five lobes.

*Leaf division.*—Simple.

*Leaf base.*—Hastate (free to slightly overlapping).

*Leaf apex.*—Broadly acute.

*Leaf venation.*—Palmate, color upper surface 143B, color lower surface 144A.

*Leaf margins.*—Palmately deeply cleft to parted into an average of five lobes, lobes are three to five lobed each with an acute apex.

*Leaf attachment.*—Petiolate.

*Leaf arrangement.*—Opposite.

*Leaf surface.*—Both surfaces slightly glossy and densely covered with short and soft adpressed hairs; average of 0.5 mm in length and too small to measure color.

*Leaf size.*—Average of 2.7 cm in length and 3 cm in width.

*Leaf color.*—Upper surface young; N137A, lower surface young; 147B, upper surface mature; N137A with a small spot 187A in center, lower surface mature; color between 138A and 147B.

*Leaf quantity.*—Average of 6 leaves per lateral branch.

*Petioles.*—Average of 7 cm in length and 1.5 mm in diameter, color 144A and occasionally tinged with 174A towards the base, surface puberulent.

*Stipules.*—2 leafy stipules are present at the base of the leaves, narrowly deltoid in shape, narrow acuminate apex, truncate base, average of 1 cm in length and 4 mm in width, color of both surfaces 157B to 157C with apex 145B, both surfaces puberulent.

Flower description:

*Inflorescence type.*—Single, rotate flowers, arranged in pairs at axillary nodes.

*Lastingness of flowers.*—About 7 days on the plant, sepals persistent.

*Flower size.*—Average of 1.3 cm in height and 4.1 cm in diameter.

*Flower fragrance.*—None.

*Flower number.*—Average of 10 flowers and buds per lateral stem and 120 per plant.

*Flower aspect.*—Upright to outward.

*Flower opening.*—About 10% open at any stage during flowering.

*Flower buds.*—Elliptic to ovate in shape, average of 1 cm in length and 5 mm in diameter, 137B in color and striped with 138C to 138D, surface densely covered with short soft adpressed hairs; 1 mm in length and NN155C to NN155D in color.

*Corolla features.*—Petals are unfused and arranged in a rotate form, slightly cupped.

*Petal number.*—5.

*Petal shape.*—Obcordate.

*Petal color.*—Opening and fully open upper surface; 75A with center and apex N78A, base N79C, primary veins N186A, secondary veins N79B to N79C, opening and fully open lower surface; N78A, base 76D, primary veins N186A, secondary veins 60A to 60B, non-fading.

*Petal surface.*—Both sides glabrous with upper side velvety.

*Petal margins.*—Entire.

*Petal apex.*—Retuse to emarginate.

*Petal size.*—Average of 2.1 cm in length and 1.9 cm in width.

*Calyx.*—Rotate and cupped, 6 mm in length and 2 cm in diameter.

*Sepals.*—5, ovate in shape with tips reflexed, average of 1.1 cm length and 4.5 mm in width, entire margin, mucronate apex, cuneate base, both surfaces are matte, color young upper surface; 143A, apex 141B, color young lower surface; 137B, striped 138C to 138D, mature upper surface; 143A, apex 141B, mature lower surface; 137B, striped 138A.

*Peduncles.*—Round in shape, average of 7.6 cm in length and 2 mm in diameter, strong, held at a 20° angle, color 144A with upper surface is strongly tinged 174B to 174C, surface puberulent.

*Pedicels.*—Round in shape, average of 2.2 cm in length and 1 mm in diameter, strong, one flower held straight to peduncle (varying between 0° and 30°), second flower in an average angle of 50° to lateral branch, color 144B, surface puberulent.

Reproductive organs:

*Gynoecium.*—1 pistil, average of 6 mm in length, 5 stigmas are decurrent (reflexed) and 187B in color, style is an average of 3 mm in length and 144B in color, ovary is 143A in color.

*Androecium.*—10 stamens, anthers are dorsifixed, oblong in shape, held at a 90° angle on top of filament, 2 mm in length, and 203B to 203C in color, filaments are 6 mm in length and N186C in color, pollen is low in quantity and 11A in color.

*Fruit/seeds.*—None detected.

It is claimed:

1. A new and distinct cultivar of *Geranium* plant named 'Noortlilac' as herein illustrated and described.

* * * * *